United States Patent [19]
Kelly et al.

[11] Patent Number: 5,571,122
[45] Date of Patent: Nov. 5, 1996

[54] UNITARY REMOVAL OF PLAQUE

[75] Inventors: Thomas L. Kelly, West Linn; Thomas A. Wiita, Lake Oswego, both of Oreg.

[73] Assignee: Endovascular Instruments, Inc., Vancouver, Wash.

[21] Appl. No.: 470,805

[22] Filed: Jun. 6, 1995

Related U.S. Application Data

[63] Continuation-in-part of Ser. No. 973,514, Nov. 9, 1992, abandoned.

[51] Int. Cl.⁶ .................................................. A61B 17/00
[52] U.S. Cl. .......................................................... 606/159
[58] Field of Search ................................ 606/159, 170, 606/171, 180, 104–108; 604/22; 128/899, 750–755

[56] References Cited

U.S. PATENT DOCUMENTS

| | | | |
|---|---|---|---|
| 4,621,636 | 11/1986 | Fogarty | 606/159 |
| 4,745,919 | 5/1988 | Bundy et al. | 606/159 |
| 5,011,490 | 4/1991 | Fischell et al. | 604/22 |
| 5,071,424 | 12/1991 | Reger | 606/170 |
| 5,078,723 | 1/1992 | Dance et al. | 606/159 |
| 5,178,625 | 1/1993 | Groshong | 606/159 |

*Primary Examiner*—Michael Powell Buiz
*Assistant Examiner*—William W. Lewis
*Attorney, Agent, or Firm*—Foster & Foster

[57] ABSTRACT

Novel apparatus and related methods are disclosed by which plaque is connected to the head of a removal instrument for removal of a unitary segment of plaque from an artery intact to increase blood flow through the artery.

32 Claims, 4 Drawing Sheets

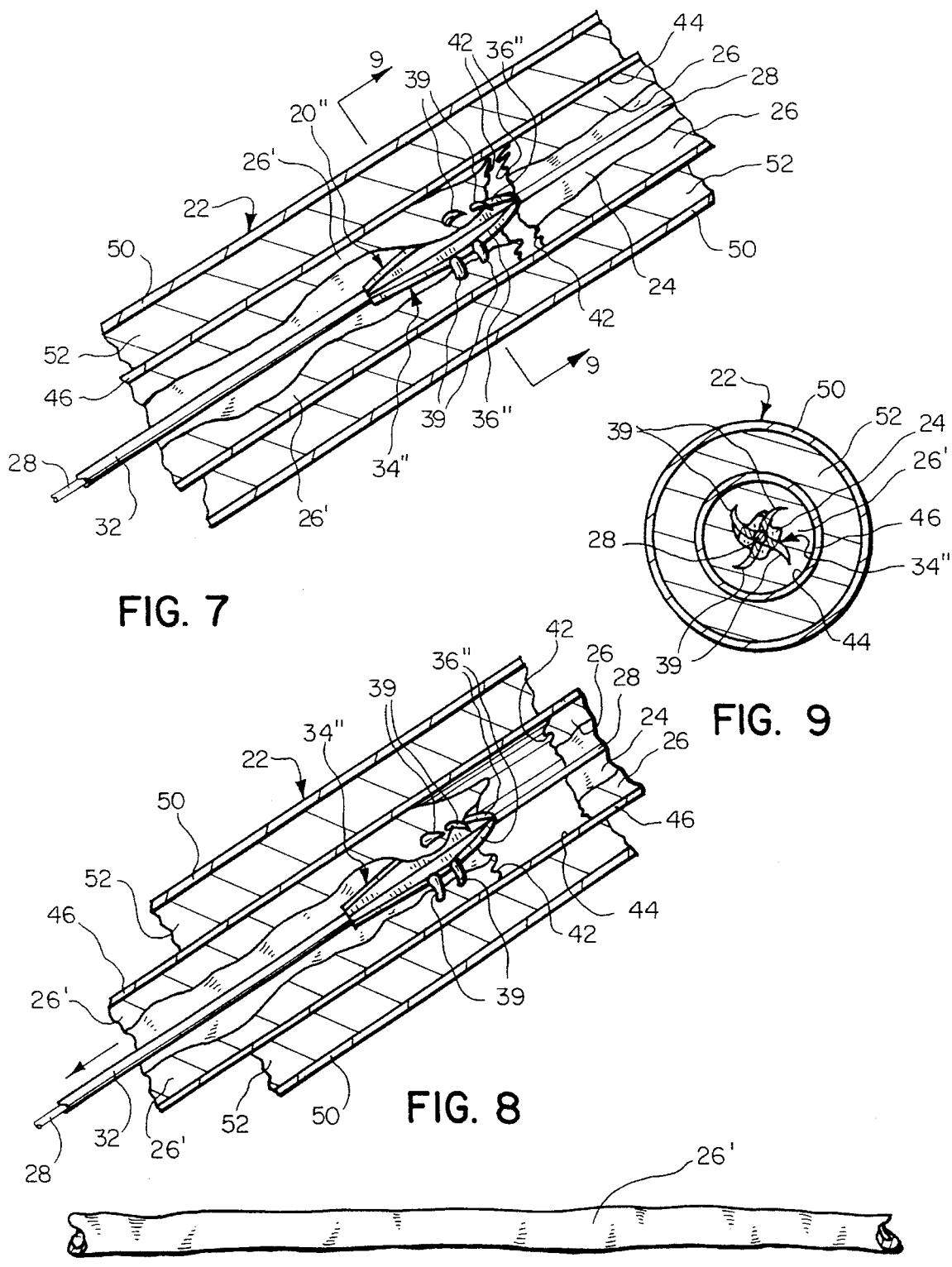

5,571,122

UNITARY REMOVAL OF PLAQUE

This application is a continuation-in-part of U.S. patent application Ser. No. 07/973,514, filed Nov. 9, 1992, now abandoned.

FIELD OF INVENTION

The present invention relates generally to increasing blood flow in arteries and, more particularly, to unitary removal of a segment of plaque from an artery.

BACKGROUND

Constricted blood flow in human arteries due to build-up of plaque is a common ailment and creates serious risks to the quality of life and, in some cases, e.g., when build-up occurs in coronary arteries, to life itself, too frequently at an early age.

Past efforts to address the problem of plaque accumulation in arteries have consisted primarily of conventional endarterectomy, by-pass surgery, dilation of the afflicted arteries using dottering or balloon angioplasty (PTA and PTCA), atherectomy, and successive severing of thin layers of plaque by reason of repeated passes of a cutting or grinding instrument along the plaque region where removal is desired. The plaque-cutting technique also requires that debris, in the form of plaque fragments released into the blood stream, be collected and removed from the artery to avoid complications (such as embolization and thrombosis). Laser removal of plaque is also known.

Conventional endarterectomy is invasive. By-pass surgery is traumatic to the tissue, very expensive, very invasive, and creates the greatest risk to the patient. Balloon angioplasty and/or dottering are often only a temporary or short-term solution, as all of the plaque in the afflicted artery at the time of treatment remains there. Dilation only rearranges plaque and may cause pieces of plaque to break loose into the blood stream. Additional build-up of plaque at the site of treatment can be prevented or alleviated by exercise and diet control, if patient compliance can be achieved. Atherectomy has demonstrated poor long-term results, at least in peripheral vessels.

Repeated cutting of the atheroma using a reciprocated instrument offers promise, but cannot be performed rapidly, may not remove all of the plaque at the treatment site, and risks complications when and if plaque fragments are not collected and thus escape to flow with blood to other parts of the cardiovascular system. Laser removal of plaque has also shown poor long-term results in some studies.

All present treatments exhibit restenosis, a complex, poorly understood process by which the artery becomes re-blocked by material that includes uncontrolled growth of smooth muscle cells (intimal hyperplasia or myointimal fibroplasia). All present treatments vary in peri-operative measures of desirability, including duration of procedure, degree of invasiveness of procedure, number and size/length of surgical incisions required, length of stay in hospital, recuperation/healing time, time until return to work, degree of anesthesia (local/general) required, overall procedure risk, and overall treatment cost.

BRIEF SUMMARY AND OBJECTS OF THE INVENTION

In brief summary, the present invention overcomes or alleviates problems of the prior art. It is believed that a less traumatic, lower risk, less expensive, less invasive, less time-consuming, and more efficacious plaque treatment apparatus and related methods are provided by which a unitary segment of plaque is removed intact from an artery.

With the foregoing in mind, it is a primary object to overcome or alleviate problems of the prior art.

A further object of paramount importance is the provision of novel plaque treatment apparatus and related methods.

Another object of value is the provision of apparatus and methodology by which a unitary segment of plaque is removed intact from an artery.

An additional object of importance is the provision of what is believed to be a significantly less traumatic, lower risk, less expensive, less invasive, less time-consuming, and more efficacious way of treating plaque.

A further object of significance is the provision of a novel plaque removal apparatus and method having one or more of the following features: (1) applicable for plaque removal in arteries of all sizes including all peripheral, coronary, and carotid arteries, (2) which can use one or two relatively small incisions, (3) which is effective with or without pre-loosening of plaque; (4) which is operable with or without a guidewire; (5) which can be placed in the artery of choice either concentrically or eccentrically; (6) usable alone or in combination without other plaque treating procedures; (7) usable in both partially and totally occluded arteries; and (8) useable in either an open surgical procedure or a percutaneous procedure.

These and other objects and features of the present invention will be apparent from the detailed description taken with reference to the accompanying drawings.

BRIEF DESCRIPTION OF THE DRAWINGS

FIG. 7 is a fragmentary longitudinal cross-section of a plaque-connecting instrument, being pulled while in a hooked position with plaque in an artery;

FIG. 8 is a fragmentary longitudinal cross-section similar to FIG. 7 showing a segment of plaque being displaced with the connecting instrument along the length of the artery;

FIG. 9 is a transverse cross-section taken along lines 9—9 of FIG. 8;

FIG. 10 is an elevational view of a segment of plaque removed intact from an artery using the present invention;

DETAILED DESCRIPTION OF THE ILLUSTRATED EMBODIMENTS

Reference is now made to the drawings wherein like numerals are used to designate like parts throughout. The present invention provides for unitary, intact removal of a segment of plaque from an artery, to resolve or alleviate constrictive blood flow problems in human arteries. The invention overcomes or alleviates health risks associated with conventional endarterectomy, by-pass surgery, dottering and balloon angioplasty procedures, atherectomy, reciprocal cutting of layers of plaque, and laser plaque removal. It is believed that intact removal of one or more segments of plaque, in accordance with the principles of the present invention, is less traumatic, creates lower risks, is less expensive, is less invasive, less time-consuming, and is more efficacious than by-pass surgery, angioplasty, and reciprocal cutting of plaque.

Figure 11:
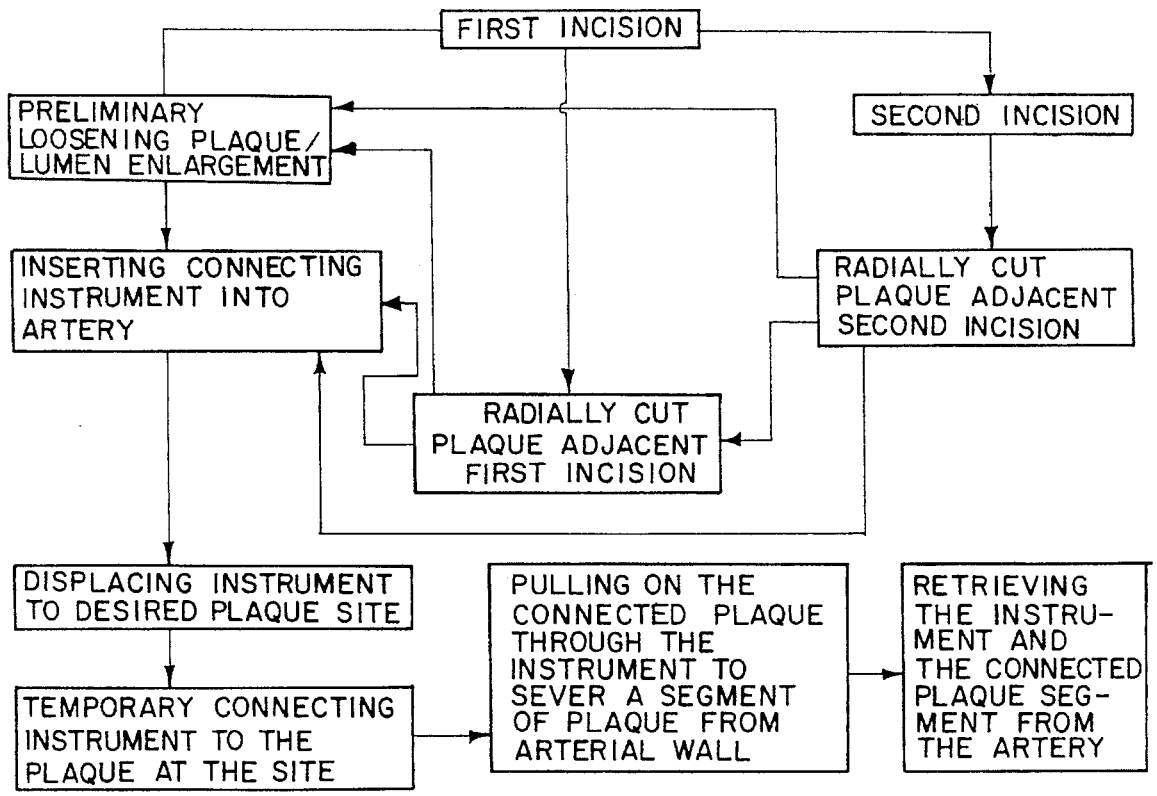
FIG. 11 is a flow chart depicting various ways of implementing the present invention.

Reference is now made to FIG. 11, for the purpose of providing a description of the present invention which is comprehensive. Initially, at least one man-made opening and in some cases only one opening is created in the artery, at a readily accessible site, for which plaque treatment is desired. This can be done conventionally, by making a small surgical incision in the artery of no greater size than needed or by making a small puncture in the vessel, such as a percutaneous puncture, followed by conventional insertion of a guidewire, which may or may not be followed by sheath insertion including insertion of a sheath particularly suitable to plaque removal.

As a preliminary to intact removal of a unitary segment of plaque, one or more plaque-loosening techniques may be employed, at the discretion of the health care provider. For example, where one incision or other man-made opening is used, the plaque adjacent thereto may be generally radially and/or circumferentially cut or bluntly dissected so as to make removal easier, sure, and predictable. Where two incisions or other man-made openings are made in the length of artery to be treated, the plaque, at both man-made openings, may be generally radially and/or circumferentially cut or bluntly dissected for ease and predictability of plaque segment removal.

If desired, a dottering instrument may be inserted and caused to vibrate and/or rotate so as to impact in a sequential fashion upon plaque adhering to the interior wall surface of the length of artery to be treated. The dottering instruments disclosed in pending U.S. Trademark application Ser. No. 07/943,514, filed Nov. 9, 1992, now abandoned (owned by the assignee of the present invention), may be utilized to so preliminarily loosen the plaque to be later unitarily removed from the artery. A second purpose for use of a dottering instrument is to enlarge the lumen or pathway to permit insertion of the plaque-connecting instrument.

Thereafter, a suitable instrument is placed, inserted, or introduced through the man-made opening into the artery, for example, although not necessarily, along an indwelling guidewire. The insertion can be generally concentric within the plaque-ridden lumen of the artery (see FIG. 1, for example) or eccentric, i.e., between the arterial wall and the plaque (see FIG. 12, for example).

After instrument insertion, instrument displacement continues, by exercise of external control, until the head of the instrument has been displaced to and located at a desired site adjacent to plaque within the artery, normally removed or remote from the insertion site. A suitable external control, which may be used in practicing the principles of the present invention, is disclosed in co-pending U.S. patent application Ser. No. 07/973,514, filed Nov. 9, 1992 (owned by the assignee of the present invention), and abandoned.

When so disposed, positioned, or placed, the head of the instrument is connected, on a temporary or releasable basis, to the adjacent plaque whereby the instrument is tethered to the plaque. The connection may be by grabbing, gripping, compressively holding, clamping, and/or embedding plaque within the head so as to bind together the plaque and the head, grasping, and/or holding the plaque by or at the head. The connection may or may not also simultaneously create a tapering interface between the engaged plaque and neighboring plaque that has not been engaged.

Once the releasable connection has been created between the head of the instrument and the adjacent plaque, the instrument is displaced so as to apply force to the tethered plaque, i.e., the plaque to which the releasable connection has been made. While the primarily force is one of pulling or stretching the plaque along the length of the artery in a direction generally parallel to the longitudinal axis of the artery and opposite to the direction of insertion, other motions may also be used. For example, the releasable connection internally within the artery may be achieved using at least some rotation and, thereafter, additional rotation may be applied in one or both directions to assist in separating a length of plaque from its adhered relation within the artery. Similarly, the head may be advanced and retracted to the same end. In some applications including two-incision situations, the plaque may be engaged and then pushed toward the second incision, rather than being pulled back toward the first incision. The direction of the insertion and force applied is independent of the arterial flow direction, i.e., it may be either antegrade or retrograde to normal blood flow.

The above-mentioned instrument displacement while the head is releasibly connected to the plaque results in tearing, severing, shearing, separating, and/or peeling instantly or progressively of a segment of plaque as a unit from the artery. The plaque segment can be separated from residual arterial plaque, including adjacent plaque by tearing or shearing or by radially and/or circumferentially cutting using a suitable instrument. Plaque may also separate along a created tapering interface due to the force transmitted through the connecting plaque as it is manipulated by the connecting instrument.

One principle at work here is that a chain is as strong as its weakest link. The force transmitted to the plaque eventually produces separation at the plane between tissue layers where the connection between the layers is weakest. In practice, this weakest connection generally occurs at the plane between the diseased tissue and the non-diseased tissue. The weakness at this plane is related to the weakness exploited using blunt dissection in conventional endarterectomy, although the physical mechanism described herein exploits this weakness in quite a different way which in no way employs the blunt dissection used in conventional endarterectomy.

The severed unitary segment of plaque is, finally, retrieved, withdrawn, and removed from the artery through the insertion site along with the instrument head to which the plaque segment is temporarily connected, or through another site toward which the head has pulled or pushed the plaque.

While the health care provider can, thereafter, insert a synthetic or biologically-obtained lining into the treated artery, the present invention comprehends as well terminating the procedure upon withdrawal of the plaque segment and removal head, followed by suitable closing of the one or more man-made openings in the artery.

The present invention comprehends provision of an apparatus for excising a segment of plaque intact from the artery which comprises an instrument equipped with a plaque-engaging head comprising a connector by which the head is temporarily joined to plaque within the artery and by which force is applied to the plaque to loosen and remove a continuous segment thereof. The instrument comprises a mechanism including an external control by which the instrument, its head, including its connector, are manipulated to locate the head adjacent the plaque to be engaged, which is normally remote from the insertion site, for temporarily or releasibly connecting the connector to the plaque without severing or fragmenting the plaque, for applying a force across the connector to the connected plaque sufficient to sever the segment of plaque intact from the artery and for removing the severed segment of plaque from the artery. A typical length of plaque so removed from an artery is illustrated in FIG. 10. The plaque segment can be short or it can be very long, for example 15–18 inches. It is, however, to be appreciated that the present invention is not restricted to any particular type of instrument. Any instrument capable of being connected to arterial plaque at a desired site and by which the connected plaque can be unitarily removed intact as a segment from the artery may be used. The form of releasable connection may be binding, snagging, compressively holding, taking hold of, grasping, grabbing, hooking, piercing, rotational engagement, clamping, biting, embedding, or in any other suitable way.

Notwithstanding the foregoing, FIGS. 1–3, 4–6, and 7–9 illustrate different mechanical configurations by which an instrument head is temporarily connected to plaque for purposes of unitary removal intact of a plaque segment. With specific reference to FIGS. 1–3, an instrument, generally designated 20, is there illustrated as having been inserted through a man-made opening in an artery, generally designated 22, in a generally concentric fashion so as to be disposed generally centrally within a lumen 24 of the artery constricted by a surface-irregular deposit of plaque 26. Insertion is illustrated as being achieved conventionally along an indwelling guidewire 28 in a collapsed or diametrically-small configuration. The instrument comprises a first relatively large tube 30 through which a smaller tube 32 generally concentrically passes. The instrument 20 comprises a head, generally designated 34 comprising a plurality of plaque connectors, each designated 36, in the form of resilient, helically-disposed blades. Each blade 36 is illustrated as being centrally enlarged at 37. The blades are joined at their respective proximal ends to the proximal portion 38 and to a distal tip 40 at their respective distal ends and may or may not pivot at their ends relative to proximal portion 38 and distal tip 40. The tube 32 extends centrally between the blades 36 and is securely non-rotatably fastened to the proximal portion of the distal tip 40.

Once the head 34, in its constricted position, is disposed at a desired location along the artery 22 adjacent a desired portion of plaque 26, an exterior control, such as the one disclosed in pending U.S. patent application Ser. No 07/973,514, filed Nov. 9, 1992, now abandoned is used to longitudinally retract tube 32 and tip 40 in respect to tube 30 causing the plaque-connector blades 36 to flex from the constricted position of FIG. 1 to the radially expanded position of FIG. 2.

Figure 2:
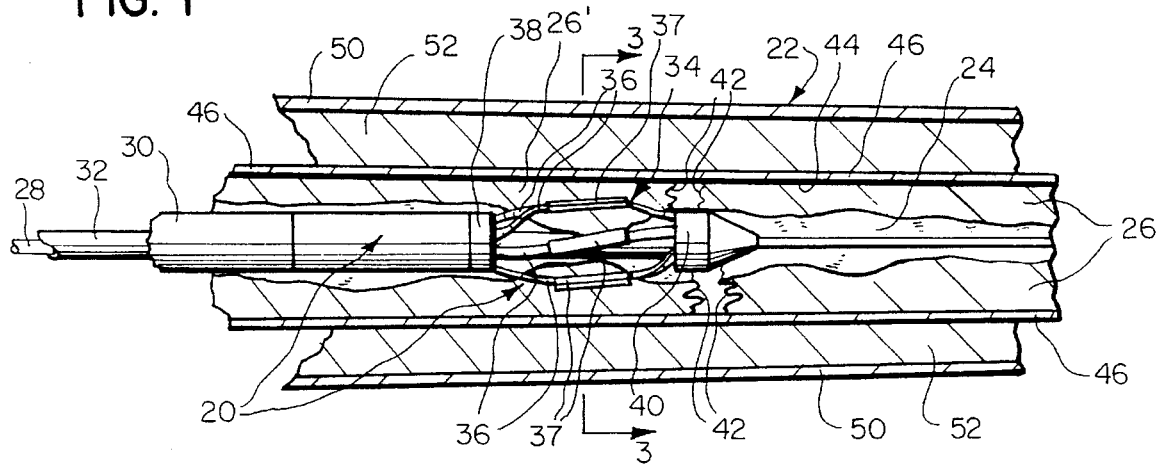
FIG. 2 is a fragmentary longitudinal cross-section illustrating the instrument being pulled while in a radially-expanded, plaque-connecting position.
Figure 3:
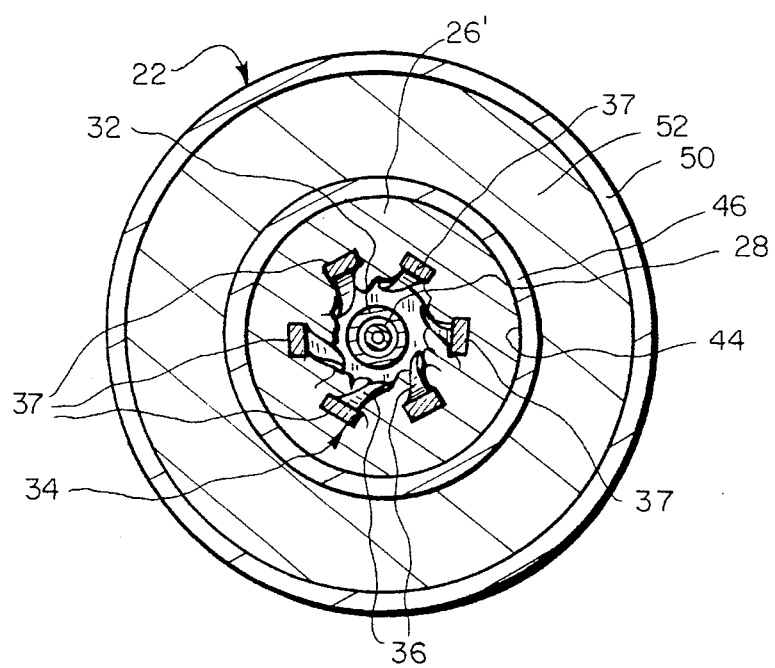
FIG. 3 is a transverse cross-section taken along lines 3—3 of FIG. 2.

Thereafter or simultaneously therewith, the head 34 is pulled and/or rotated so as to create a releasible or temporary connection between the head 34 and the plaque engaged by the blades 36, as shown in FIG. 3. This grasping, grabbing, clamping, binding or like phenomenon causes the connected plaque to move as the instrument head 34 is moved by manipulation of the external control. Thus, the head 34 can be moved back and forth and/or can be rotated in one or the other or both directions so as to radially and/or circumferentially sever or shear the plaque from itself, as illustrated at site 42 in FIG. 2. The instrument 20 and its head 34 are retracted in a generally longitudinal or axial direction, either alone or in conjunction with back/and forth movement as well as selected rotational movement in one or the other, or both directions. This causes the plaque to be sheared, peeled, or be severed from the internal surface 44 of the internal wall 46 of the artery 22, which defines the boundary between the arterial wall and the engaged plaque. It is to be appreciated that as arterial disease progresses, this boundary between the diseased and undiseased arterial wall may be located within the interior layer 46, or between layers 46 and 52, or within layer 52, but does not generally invade layer 50. The severed unitary plaque segment 26' is retrieved together with the connected head 34 and removed through the man-made opening in the artery and when removed and disconnected from the head has a worm-like appearance as shown in FIG. 10. Plaque segment 26' might be called an endarterectomy plug. Medically speaking, it is by definition an endarterectomy plug, although the endarterectomy has been achieved by novel, non-conventional techniques.

In medical terms, the artery 22 comprises an outside layer 50 known as the tunica adventitia, a central, radially larger intermediate layer 52, known as the tunica media, and the previously mentioned interior layer or wall 46, known as the tunica intima endothelium. The plaque 26 is typically referred to as atherosclerotic plaque, which in advanced stages of disease such as are typically treated, partially or wholly, engulfs the tunica media.

The present invention, as stated earlier, does not contemplate cutting, grinding, or fragmenting pieces of plaque 26 from the atheroma, but rather is directed to grasping, gripping, clamping, or otherwise releasibly connecting the instrument head to the plaque for intact removal of a segment of plaque and in certain embodiments, including the embodiments disclosed herein, contemplates simultaneously creating a tapered interface. The creation of the tapered interface is advantageous in that, after the treatment when flow is restored, a tapered interface in the upstream direction will help prevent the creation of undesirable flaps of disease being lifted from the vessel wall, as the flow over the tapered disease will press the disease more firmly into the vessel wall, and also reduce flow turbulence at the interface.

Figure 4:
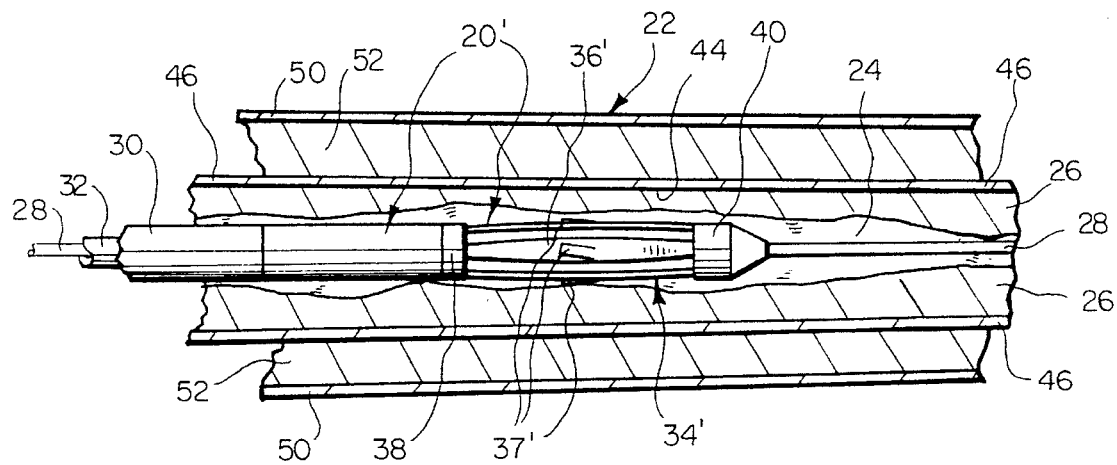
FIG. 4 is a fragmentary longitudinal cross-section of a second plaque-connecting instrument, in a diametrally-constricted orientation, disposed in a plaque-ladened artery.
Figure 5:
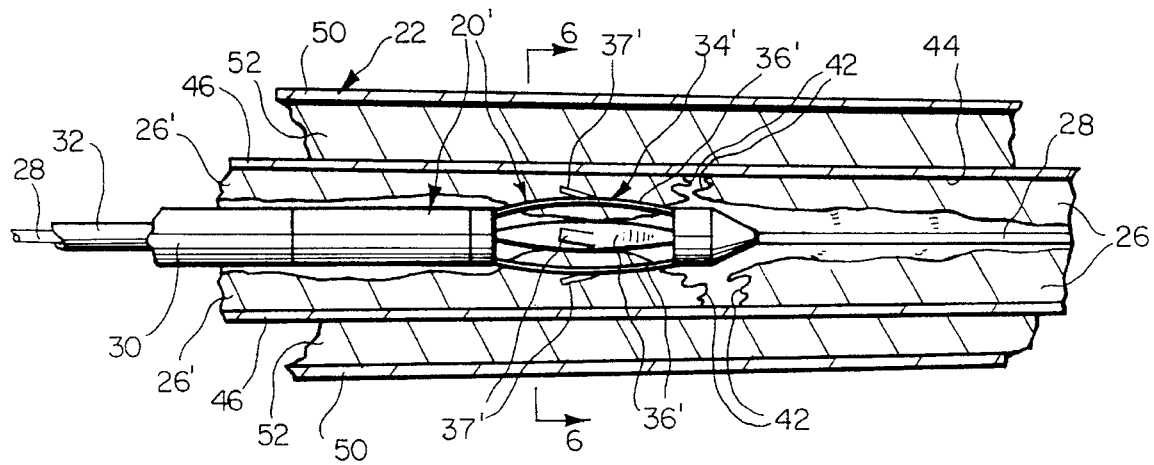
FIG. 5 is a fragmentary longitudinal cross-section illustrating the instrument being pulled while in a radially-expanded plaque-connecting position.
Figure 6:
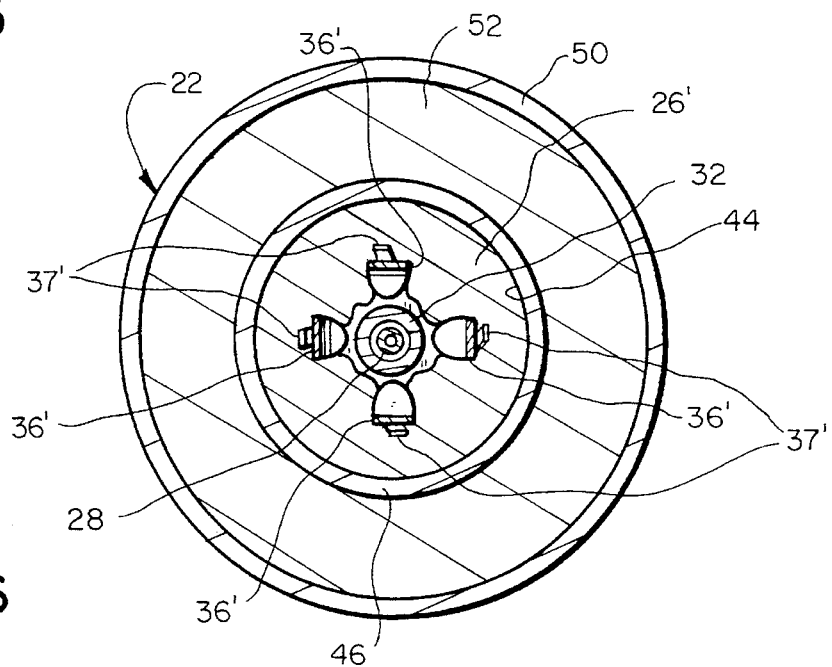
FIG. 6 is a transverse cross-section taken along lines 6—6 of FIG. 5.

Reference is now made to the instrument illustrated in FIGS. 4–6, which is generally designated 20'. The instrument 20' is connected and controlled as is the above-described instrument 20. Only differences between instrument 20 and instrument 20' need description here. The numerals used in FIGS. 4–6 which are identical to numerals used in FIGS. 1–3 identify identical or substantially identical parts. The instrument 20' differs from the instrument 20 primarily in the configuration of connector head 34'. Head 34' comprises a plurality of spaced, somewhat longitudinally-extending blades 36' anchored, respectively, at the proximal ends 38 thereof to the distal portion of the tube 30 and non-rotatably joined to the tip 40. Each blade 36' comprises a proximally-directed barb 37'. While each barb 37' is illustrated as being disposed at a slight acute angle in respect to the longitudinal axis of the artery 22, any suitable barb orientation may be used.

When the tube 32 is retracted by the external control in respect to tube 30, tip 40 is displaced toward proximal portion 38, causing the blades 36' of the head or connector 34' to flex radially outwardly. Withdrawal (retraction) and/or rotation of the head 34' causes the blades 36' to bite into, but not sever away pieces of the plaque 26. Generally longitudinal retraction of the instrument 20', including connecting head 34' with the plaque 26 bindingly connected between the blades 36', accommodates severing or shearing of the plaque at radially-directed site 42 thereby separating plaque segment 26' from residual arterial plaque 26. This severing or shearing can create a tapered or beveled interface. The retraction of the instrument 20' may be accompanied by to and fro longitudinal movement of the head 34', retraction only and/or rotation in one or the other or both directions sufficient to sever, shear, or peel the plaque segment 26' from the annular interface 44 of the inner layer 46 of the artery 22, or at whatever depth the diseased/non-diseased interface has progressed, as described earlier.

The severed plaque segment 26' is retrieved and removed from the artery through a man-made opening therein as the instrument 20' is removed, the head 34' remaining releasibly connected to the plaque segment 26' during retrieval and removal.

Reference is now made to the unitary plaque segment removal instrument, generally designated 20", illustrated in FIGS. 7–9. To the extent parts of instrument 20" illustrated in FIGS. 7–9 are identical or substantially identical to parts previously described in connection with FIGS. 1–3, identical numerals are used and no further description thereof is necessary.

Tube 30 and distal portion 38 thereof do not form a part of the embodiment illustrated in FIGS. 7–9. Instrument head 34" is non-rotatably secured at the distal end of tube 32 and is inserted into the desired location along guidewire 28. The instrument head 34" is illustrated as maintaining a constant transverse dimensional configuration.

Head 34" comprises a plurality of curvilinear blades 36", each of which is illustrated as carrying a pair of curved hooks 39, which engage the plaque when rotated so as to pierce portions thereof without severing pieces of plaque therefrom. Thereafter, by displacing the head 34" to and fro, or by retracting alone and/or rotationally as desired and by primarily retracting the head 34" along the length of the artery 22, plaque segment 26' is loosened, severed, retrieved, and removed from the artery through a man-made opening therein.

Figure 1:
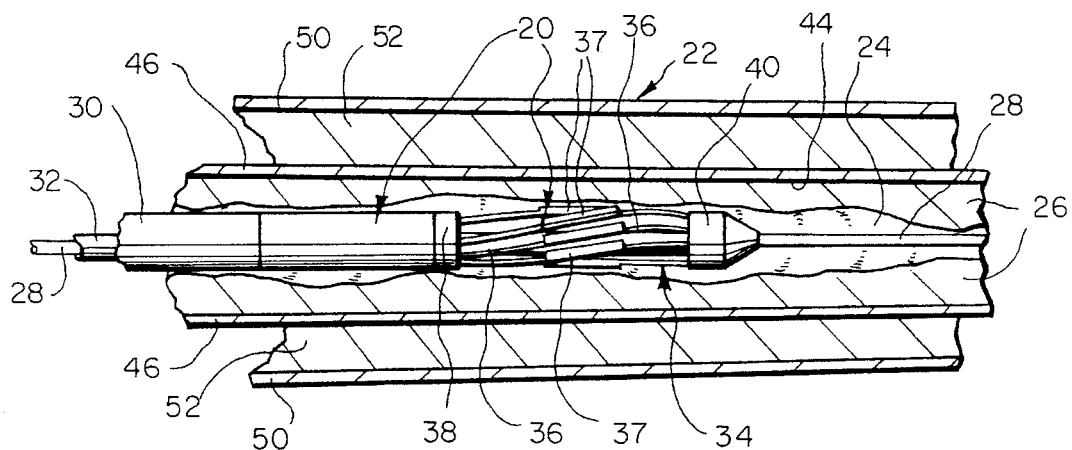
FIG. 1 is a fragmentary longitudinal cross-section of a plaque-connecting instrument, in diametrally-constricted orientation, disposed in a plaque-ladened artery.
Figure 12:
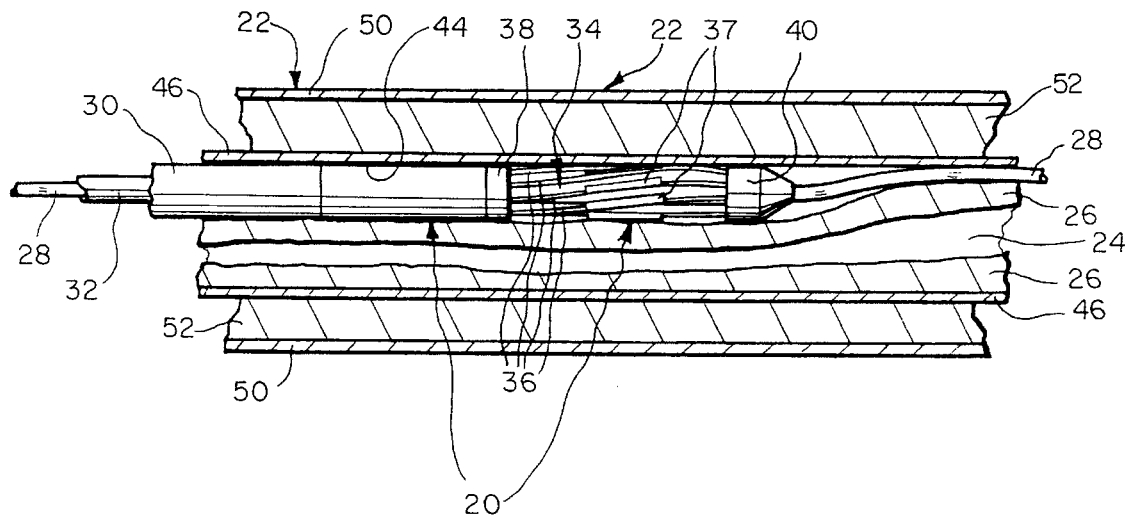
FIG. 12 is a fragmentary longitudinal cross-section of the plaque-connecting instrument eccentrically or asymmetrically inserted into an artery, i.e., between the inner arterial wall and the plaque.

Reference is now made to FIG. 12, which illustrates the same apparatus as shown in FIGS. 1–3, illustrating placement of the instrument head 34 into the artery between the plaque 26 and the arterial wall surface or cleavage interface of weakness 44 and advanced along the arterial surface 44 to the desired plaque connection site without prior use of an interface separation tool.

The invention may be embodied in other specific forms without departing from the spirit of essential characteristics thereof. The present embodiments therefore to be considered in all respects as illustrative and are not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A method of excising plaque from an artery comprising the steps of:

inserting an instrument into the artery, the artery having an axis;

placing the instrument adjacent to plaque in the artery;

grasping the plaque with the instrument without materially cutting the plaque by the instrument;

maintaining grasp while displacing the instrument along the axis of the artery thereby generally axially dislodging a length of plaque from the artery;

removing the dislodged length of plaque from the artery.

2. A method of removing arterial plaque comprising the steps of:

grabbing hold of plaque within an artery with a removal instrument;

applying force to the plaque generally along the length of the artery to sever without longitudinally cutting a segment of plaque from a portion of a wall of the artery;

withdrawing the plaque segment from the artery.

3. A method of increasing blood flow in an artery comprising the steps of:

introducing a gripping instrument into an artery through a man-made opening therein;

displacing the gripping instrument along the artery to a site where the artery is obstructed at least in part by plaque;

gripping plaque at the site with the gripping instrument;

tearing plaque from the artery without cutting the plaque along the axis of the artery by displacing the instrument while the instrument is gripping the plaque;

removing the instrument and the gripped plaque through the man-made opening.

4. A method of increasing blood flow in an artery comprising the steps of:

tethering arterial plaque to an indwelling instrument at a site within the artery with immaterial axial cutting of tethered plaque, pulling the instrument and plaque along the length of the artery thereby forcibly tearing a segment of plaque, in the direction of the length of the artery, from a portion of the artery and removing the torn plaque segment from the artery.

5. A method of treating plaque in an artery having an elongated length to increase blood flow comprising the steps of:

inserting a connecting head into an artery;

locating the head adjacent to plaque within the artery;

removably connecting the head to the plaque without cutting plaque from the artery along its length;

pulling on the plaque through the head thereby severing a segment of plaque intact from the artery;

retrieving the head and connected severed segment of plaque from the artery.

6. A method according to claim 5 wherein the inserting step is preceded by creating at least one man-made opening in the artery.

7. A method according to claim 6 wherein the inserting step comprises placing a guidewire through the opening and advancing the head into the artery along the guidewire.

8. A method according to claim 5 wherein the inserting step is preceded by preliminarily loosening the plaque.

9. A method according to claim 8 wherein the loosening step comprises making at least one radial cut in the plaque.

10. A method according to claim 5 wherein the locating step comprises placing the head within a central lumen of the artery.

11. A method according to claim 5 wherein the removably connecting step comprises taking hold of the plaque by the head.

12. A method according to claim 5 wherein the removably connecting step comprises grasping the plaque by the head.

13. A method according to claim 5 wherein the removably connecting step comprises grabbing the plaque by the head.

14. A method according to claim 5 wherein the removably connecting step comprises engaging the plaque by the head.

15. A method according to claim 5 wherein the severing step comprises shearing the plaque intact from a wall of the artery.

16. A method according to claim 5 wherein the retrieving step comprises removing the head and the severed segment of plaque from the artery.

17. A method according to claim 5 wherein the removably connecting step comprises hooking the plaque with the head.

18. A method according to claim 5 wherein the removably connecting step comprises piercing the plaque with the head.

19. A method according to claim 5 wherein the removably connecting step occurs due to rotating the head.

20. A method according to claim 19 wherein the rotating step comprises causing the head to bindingly bite into the plaque.

21. A method according to claim 19 wherein the rotating step comprises embedding plaque within the head in binding relation.

22. A method according to claim 5 wherein the removably connecting step comprises binding the plaque and the head together.

23. A method according to claim 5 wherein the removably connecting step comprises snagging the plaque with the head.

24. A method according to claim 5 wherein the locating step comprises advancing the head to an arterial location remote from the insertion site.

25. A method of treating plaque in an artery to increase blood flow comprising the steps of:

preliminarily loosening the arterial plaque by subjecting the plaque to be removed to dottering;

inserting a connecting head into an artery;

locating the head adjacent to plaque within the artery;

removably connecting the head to the plaque;

pulling on the plaque through the head thereby severing a segment of plaque intact from the artery;

retrieving the head and connected severed segment of plaque from the artery.

26. A method of treating plaque in an artery to increase blood flow comprising the steps of:

preliminarily displacing the plaque by subjecting the plaque to be removed to balloon angioplasty;

inserting a connecting head into an artery;

locating the head adjacent to plaque within the artery;

removably connecting the head to the plaque;

pulling on the plaque through the head thereby severing a segment of plaque intact from the artery;

retrieving the head and connected severed segment of plaque from the artery.

27. A method of treating plaque in an artery to increase blood flow comprising the steps of:

inserting a connecting head into an artery;

locating the head adjacent to plaque within the artery by placing the head within the artery between the plaque and a wall of the artery so that insertion of the head separates in part the plaque and the artery at the interface between the two;

removably connecting the head to the plaque;

pulling on the plaque through the head thereby severing a segment of plaque intact from the artery;

retrieving the head and connected severed segment of plaque from the artery.

28. A method of treating plaque in an artery to increase blood flow comprising the steps of:

inserting a connecting head into an artery;

locating the head adjacent to plaque within the artery;

removably connecting the head to the plaque by compressively holding the engaged plaque at the head;

pulling on the plaque through the head thereby severing a segment of plaque intact from the artery;

retrieving the head and connected severed segment of plaque from the artery.

29. A method of treating plaque in an artery to increase blood flow comprising the steps of:

inserting a connecting head into an artery;

locating the head adjacent to plaque within the artery;

removably connecting the head to the plaque;

pulling on the plaque through the head by stretching the plaque thereby severing a segment of plaque intact from the artery;

retrieving the head and connected severed segment of plaque from the artery.

30. A method of treating plaque in an artery to increase blood flow comprising the steps of:

inserting a connecting head into an artery;

locating the head adjacent to plaque within the artery;

removably connecting the head to the plaque;

pulling on the plaque through the head thereby severing a segment of plaque intact from the artery by progressively peeling the plaque intact from a wall of the artery;

retrieving the head and connected severed segment of plaque from the artery.

31. A method of treating plaque in an artery to increase blood flow comprising the steps of:

inserting a connecting head into an artery;

locating the head adjacent to plaque within the artery;

removably connecting the head to the plaque;

pulling on the plaque through the head thereby severing a segment of plaque intact from the artery by both separating the plaque segment from other plaque within the artery and separating the plaque segment from a wall of the artery;

retrieving the head and connected severed segment of plaque from the artery.

32. A method of treating plaque in an artery to increase blood flow comprising the steps of:

inserting a connecting head into an artery;

locating the head adjacent to plaque within the artery;

removably connecting the head to the plaque by clamping the head to the plaque;

pulling on the plaque through the head thereby severing a segment of plaque intact from the artery;

retrieving the head and connected severed segment of plaque from the artery.

* * * * *